(12) United States Patent
Vik et al.

(10) Patent No.: US 8,879,817 B2
(45) Date of Patent: Nov. 4, 2014

(54) SCAN PLAN FIELD OF VIEW ADJUSTOR, DETERMINER, AND/OR QUALITY ASSESSOR

(71) Applicant: Koninklijke Philips N.V., Eindhoven (NL)

(72) Inventors: Torbjorn Vik, Hamburg (DE); Jorg Bredno, Briarcliff Manor, NY (US); Rafael Wiemker, Kisdorf (DE); Mark E. Olszewski, Solon, OH (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/187,558

(22) Filed: Feb. 24, 2014

(65) Prior Publication Data

US 2014/0169652 A1  Jun. 19, 2014

Related U.S. Application Data

(63) Continuation of application No. 13/508,370, filed as application No. PCT/IB2010/054664 on Oct. 14, 2010, now Pat. No. 8,699,768.

(60) Provisional application No. 61/261,463, filed on Nov. 16, 2009.

(51) Int. Cl.
| | | |
|---|---|---|
| *G06K 9/00* | (2006.01) | |
| *A61B 6/03* | (2006.01) | |
| *G06T 7/00* | (2006.01) | |
| *A61B 6/00* | (2006.01) | |
| *A61B 9/00* | (2006.01) | |
| *A61B 5/00* | (2006.01) | |
| *A61B 6/12* | (2006.01) | |
| *A61B 5/055* | (2006.01) | |

(52) U.S. Cl.
CPC ............... *G06T 7/0012* (2013.01); *A61B 6/032* (2013.01); *A61B 5/7207* (2013.01); *G06T 2207/10081* (2013.01); *G06T 7/0032* (2013.01); *A61B 6/488* (2013.01); *G06T 7/0026* (2013.01); *G06T 2207/30004* (2013.01); *A61B 6/12* (2013.01); *A61B 5/055* (2013.01); *A61B 6/5264* (2013.01)
USPC ................................ 382/131; 382/296; 378/4

(58) Field of Classification Search
USPC ......... 382/100, 103, 106–107, 128–134, 154, 382/162, 168, 173, 181, 193–194, 199, 232, 382/254, 274, 276, 286, 291, 305, 312, 382/294–298; 378/4, 5, 8, 21
See application file for complete search history.

(56) References Cited

U.S. PATENT DOCUMENTS

| | | | | |
|---|---|---|---|---|
| 5,457,724 | A * | 10/1995 | Toth | 378/4 |
| 5,878,102 | A * | 3/1999 | Kalvin | 378/4 |
| 6,023,495 | A * | 2/2000 | Adler et al. | 378/4 |

(Continued)

FOREIGN PATENT DOCUMENTS

| | | | | |
|---|---|---|---|---|
| WO | 2008015611 | * | 2/2008 | A61B 6/00 |
| WO | 2008015611 A2 | | 2/2008 | |

(Continued)

*Primary Examiner* — Seyed Azarian

(57) ABSTRACT

A method includes using a pre-scan image to define a scan field of view for a region of interest of a patient to be scanned for at least one image acquisition of a series of image acquisitions of a scan plan, performing an image acquisition of the series based on a corresponding scan field of view for the image acquisition, and determining, via a processor (120), a next field of view for a next image acquisition of the series based on available image related data.

20 Claims, 10 Drawing Sheets

(56) References Cited

U.S. PATENT DOCUMENTS

Figure 1:
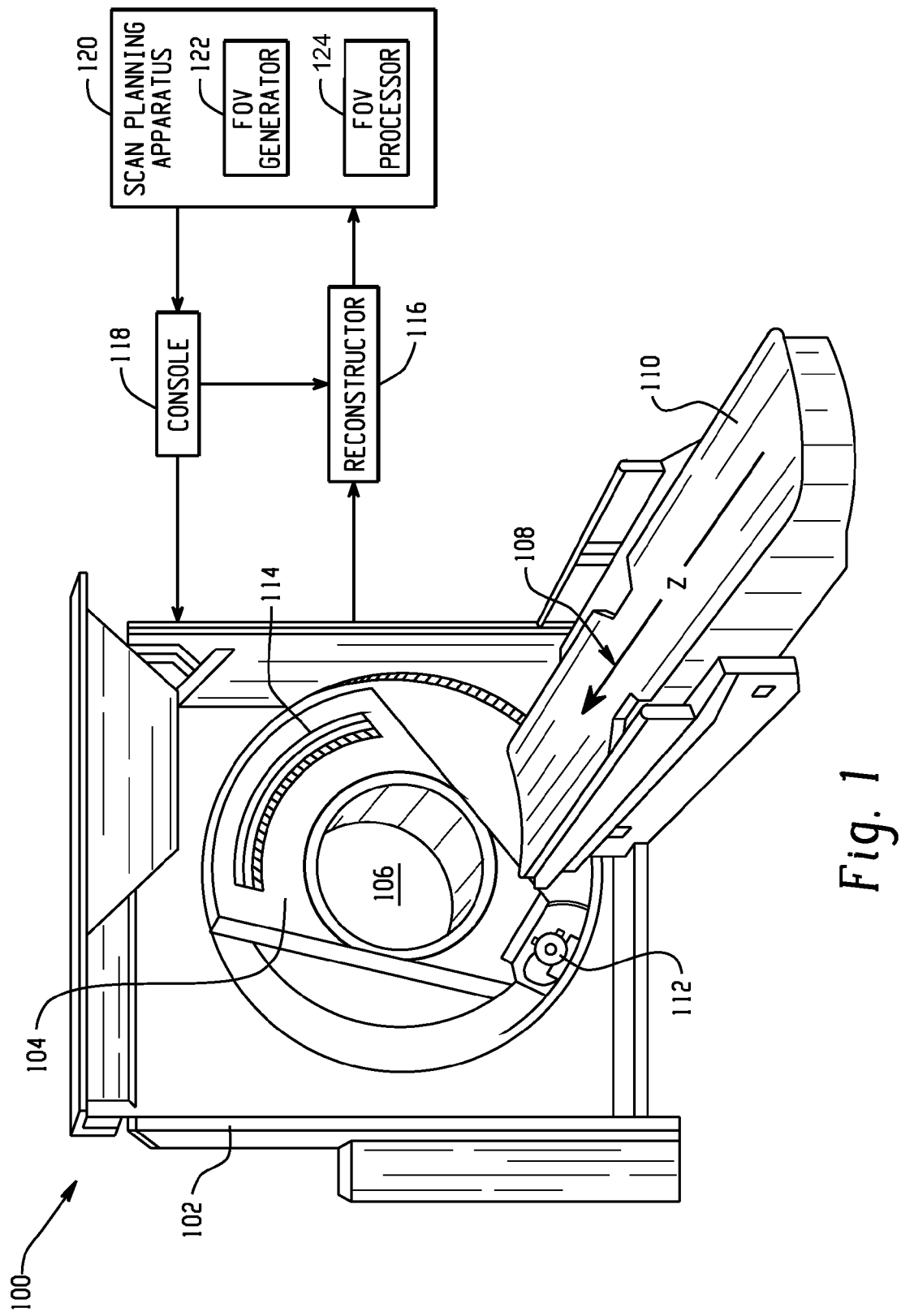

| | | | |
|---|---|---|---|
| 6,256,368 B1 * | 7/2001 | Hsieh et al. | 378/8 |
| 2005/0004446 A1 | 1/2005 | Cowan et al. | |
| 2009/0161937 A1 * | 6/2009 | Peng et al. | 382/131 |

FOREIGN PATENT DOCUMENTS

| | | |
|---|---|---|
| WO | 2008139374 A1 | 11/2008 |
| WO | 2008155738 A2 | 12/2008 |
| WO | 2009050676 A1 | 4/2009 |

* cited by examiner

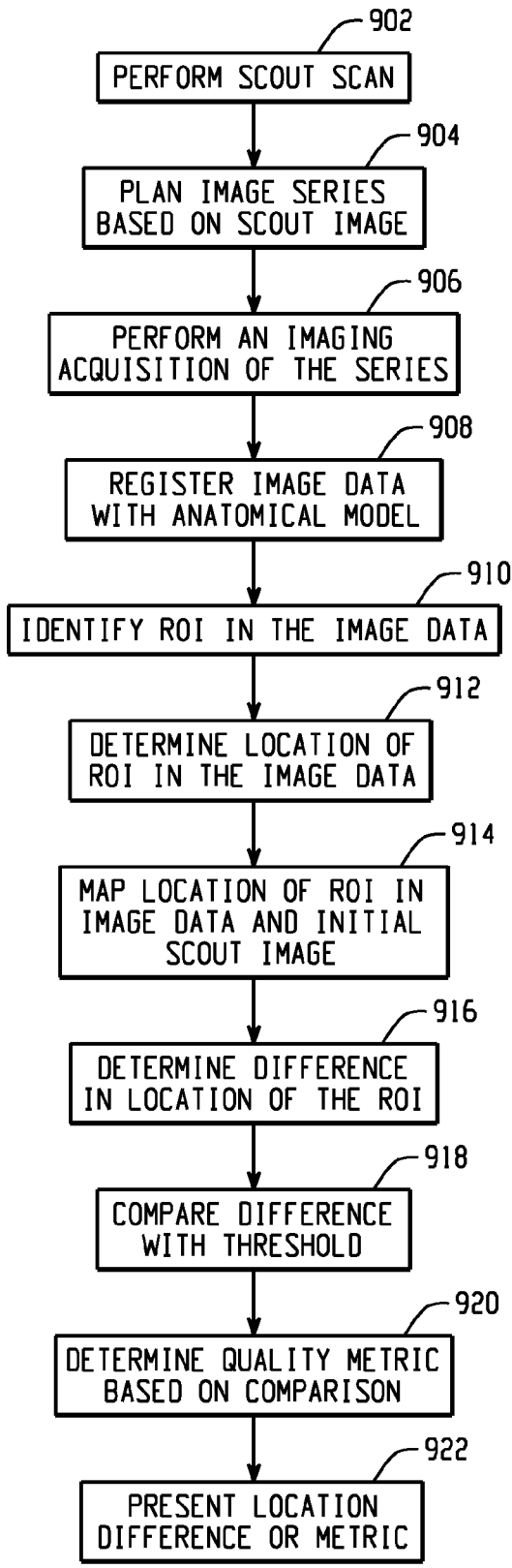
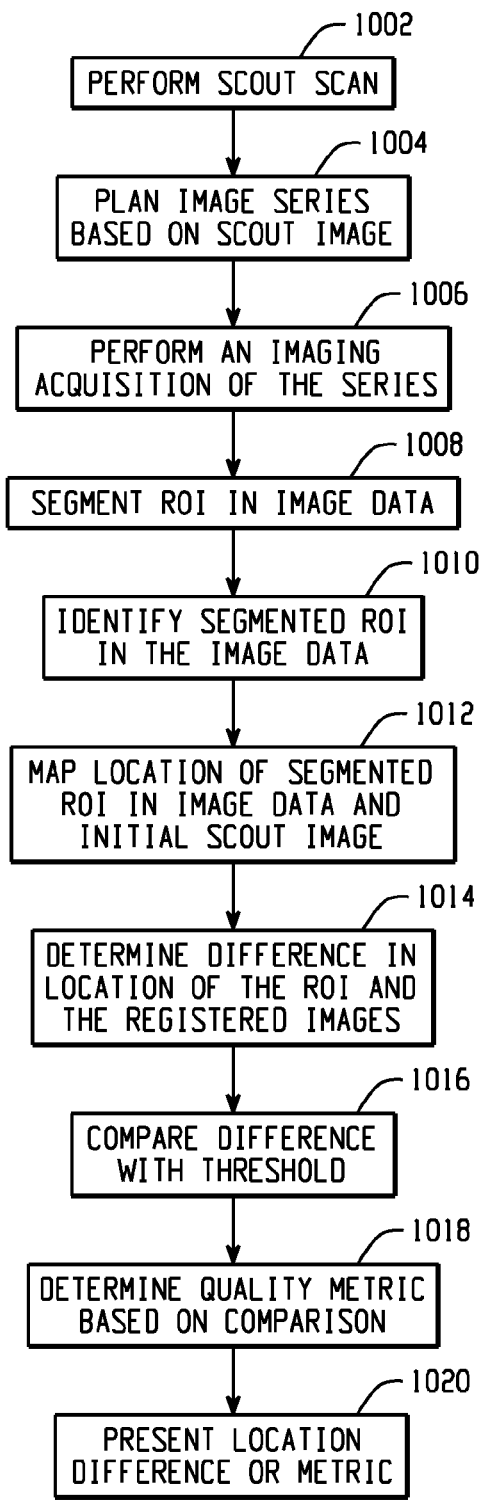
Fig. 9
Fig. 10

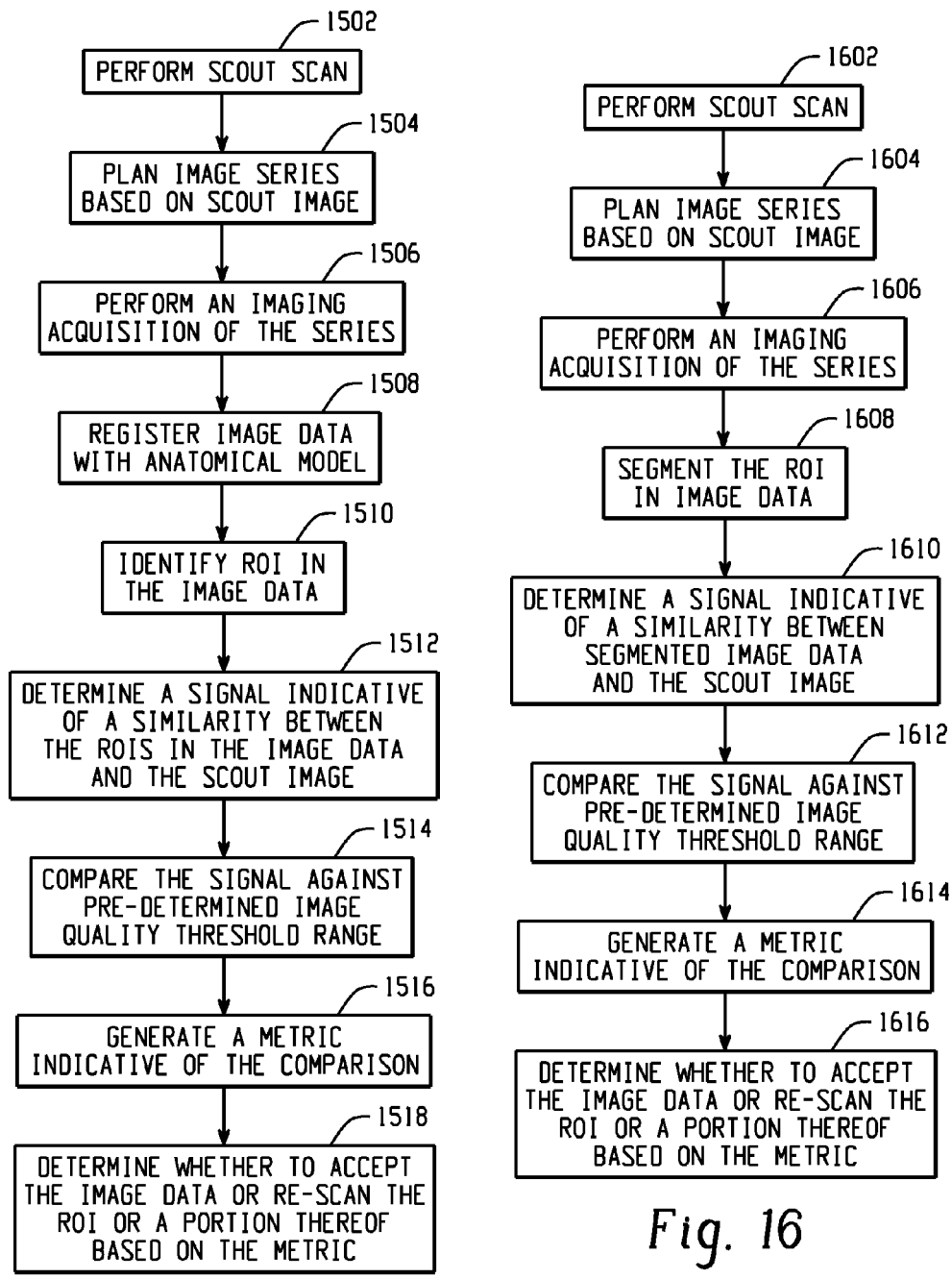

SCAN PLAN FIELD OF VIEW ADJUSTOR, DETERMINER, AND/OR QUALITY ASSESSOR

CROSS REFERENCE TO RELATED APPLICATIONS

This application is a continuation of application Ser. No. 13/508,370, filed May 7, 2012, which is a national filing of PCT application Serial No. PCT/IB2010/054664, filed Oct. 14, 2010, published as WO 2011/058461 A1 on May 19, 2011, which claims the benefit of U.S. provisional application Ser. No. 61/261,463 filed Nov. 16, 2009, which is incorporated herein by reference.

The following generally relates to scan planning and is described with particular application to computed tomography (CT). However, it also amenable to other applications such as magnetic resonance imaging (MRI), interventional X-ray, and other imaging applications.

A computed tomography (CT) scanner includes an x-ray tube mounted on a rotatable gantry that rotates around an examination region about a longitudinal or z-axis. The x-ray tube emits ionizing radiation that traverses the examination region and irradiates a patient therein. A detector array subtends an angular arc opposite the examination region from the x-ray tube. The detector array detects radiation that traverses the examination region and generates projection data indicative thereof. A reconstructor processes the projection data and reconstructs volumetric image data indicative thereof. The volumetric image data is processed to generate one or more images of the patient.

Prior to imaging a patient with such a scanner, a scan plan is generated. A typical scan plan defines, among other parameters, a scan field of view (FOV). In instances in which the scan plan includes multiple image acquisitions (e.g., a non-contrast study followed by a contrast study followed by . . . ), planning includes defining one or more FOVs for each of the image acquisitions based on one or more initial scout images, often showing the patient in lateral and frontal projection. Unfortunately, the patient generally does not remain stationary from the time of the scout scan to the last image acquisition. As a result, the actual location of the region of interest in the examination region over time may not be well reflected in the initial scout image, which was used to plan the FOVs. Consequently, depending on the movement, a planned scan FOV may no longer be a desired FOV as it may no longer cover or suitably cover the region of interest to be scanned.

One approach to determining whether a planned scan FOV is still the desired FOV for an image acquisition is to inspect visually data from a previously performed data acquisition of the series of acquisitions, especially for image acquisitions with higher x-ray and/or contrast agent burden to the patient. This is often performed before each subsequent imaging procedure, and the planned FOV is manually tweaked (e.g., the couch position is manually adjusted to re-align the FOV and hence the region of interest in the examination zone) when the planned scan FOV does not represent the desired FOV. This approach introduces operator-variability into the study and requires operator interaction between scans, which can increase the amount of time between scans and can render the study more susceptible to patient movement. This reduces the opportunity for use of standardized imaging protocols.

Aspects of the present application address the above-referenced matters and others.

According to one aspect, a method includes using a pre-scan image to define a scan field of view for a region of interest of a patient to be scanned for at least one image acquisition of a series of image acquisitions of a scan plan, performing an image acquisition of the series based on a corresponding scan field of view for the image acquisition, and determining, via a processor, a next field of view for a next image acquisition of the series based on available image related data.

In another embodiment, a scan planning apparatus includes a field of view generator that defines a scan field of view for a region of interest of a patient for at least one image acquisition of a series of image acquisitions of a scan plan based on a pre-scan image and a field of view processor that determines a next field of view for a next image acquisition of the series based on available image related data.

In another embodiment, a computer readable storage medium includes instructions which, when executed by a computer, cause the computer to perform various acts such as using a pre-scan image to define a scan field of view for a region of interest of a patient for at least one image acquisition of a series of image acquisitions of a scan plan; performing an image acquisition of the series based on the first scan field of view, and determining a next field of view for a next image acquisition of the series based on available image related data.

The invention may take form in various components and arrangements of components, and in various steps and arrangements of steps. The drawings are only for purposes of illustrating the preferred embodiments and are not to be construed as limiting the invention.

FIG. 1 illustrates an example imaging system in connection with a scan planning apparatus with at least a FOV processor.

Figure 2:
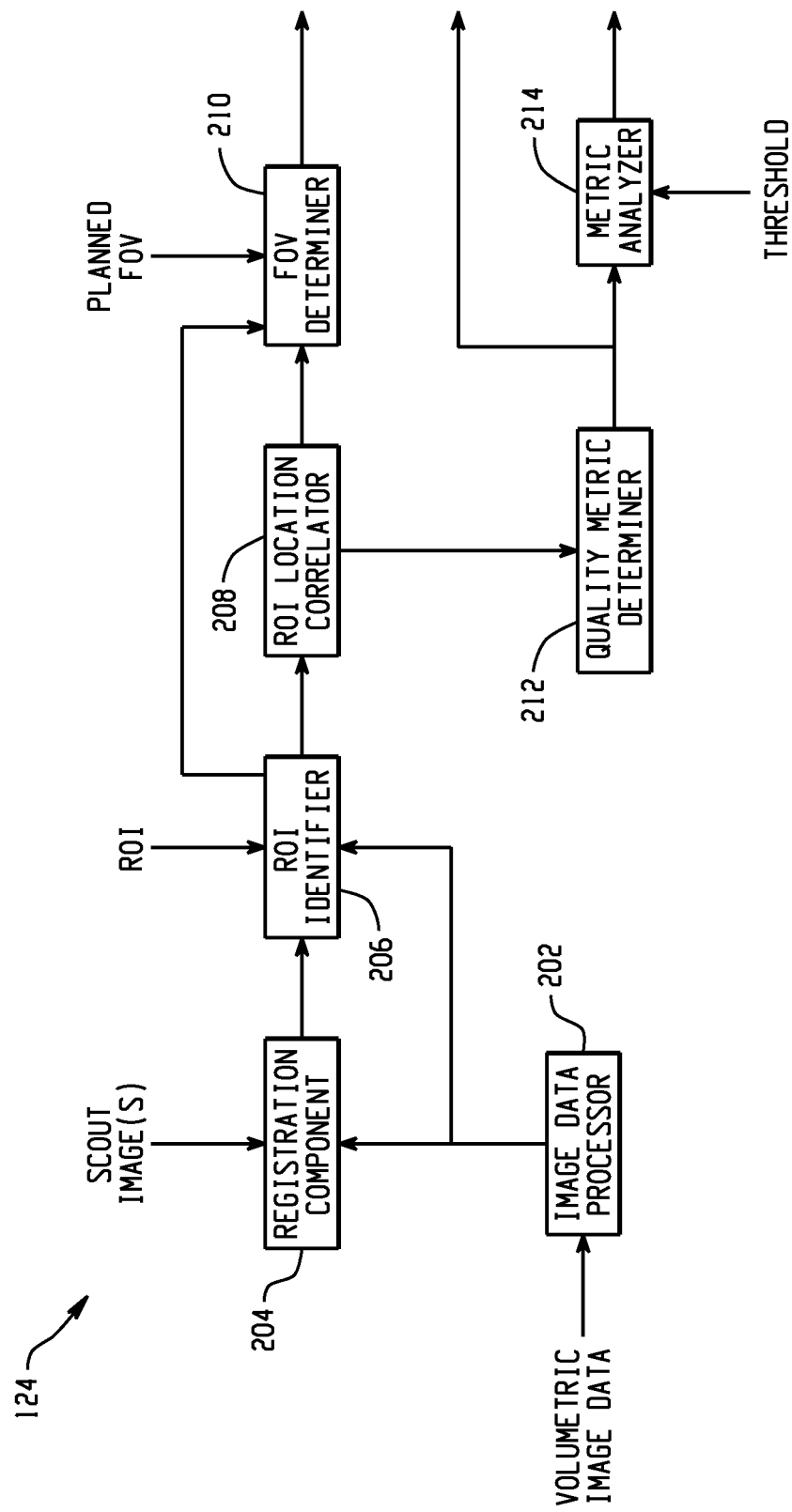
Figure 3:
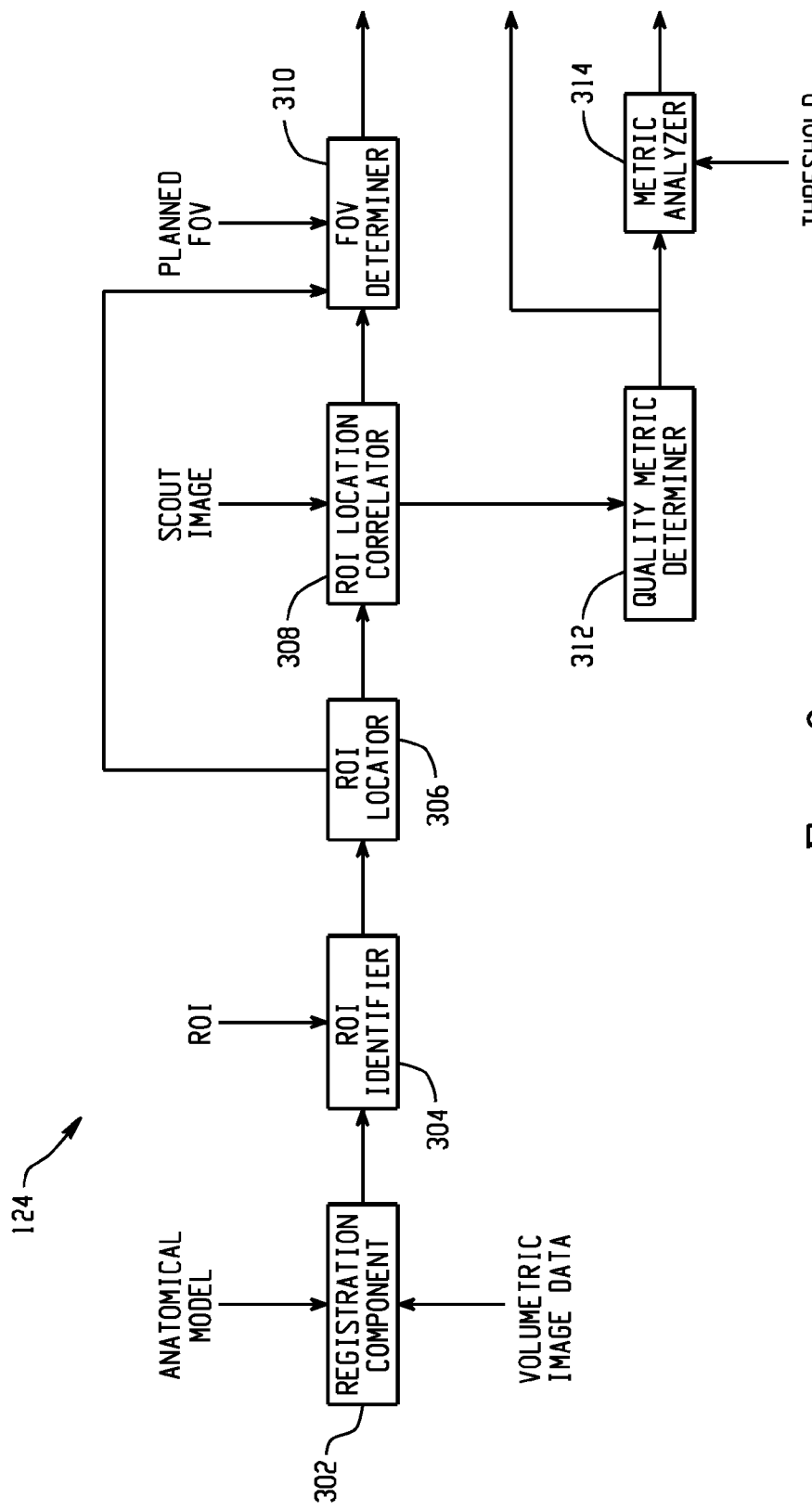
Figure 4:
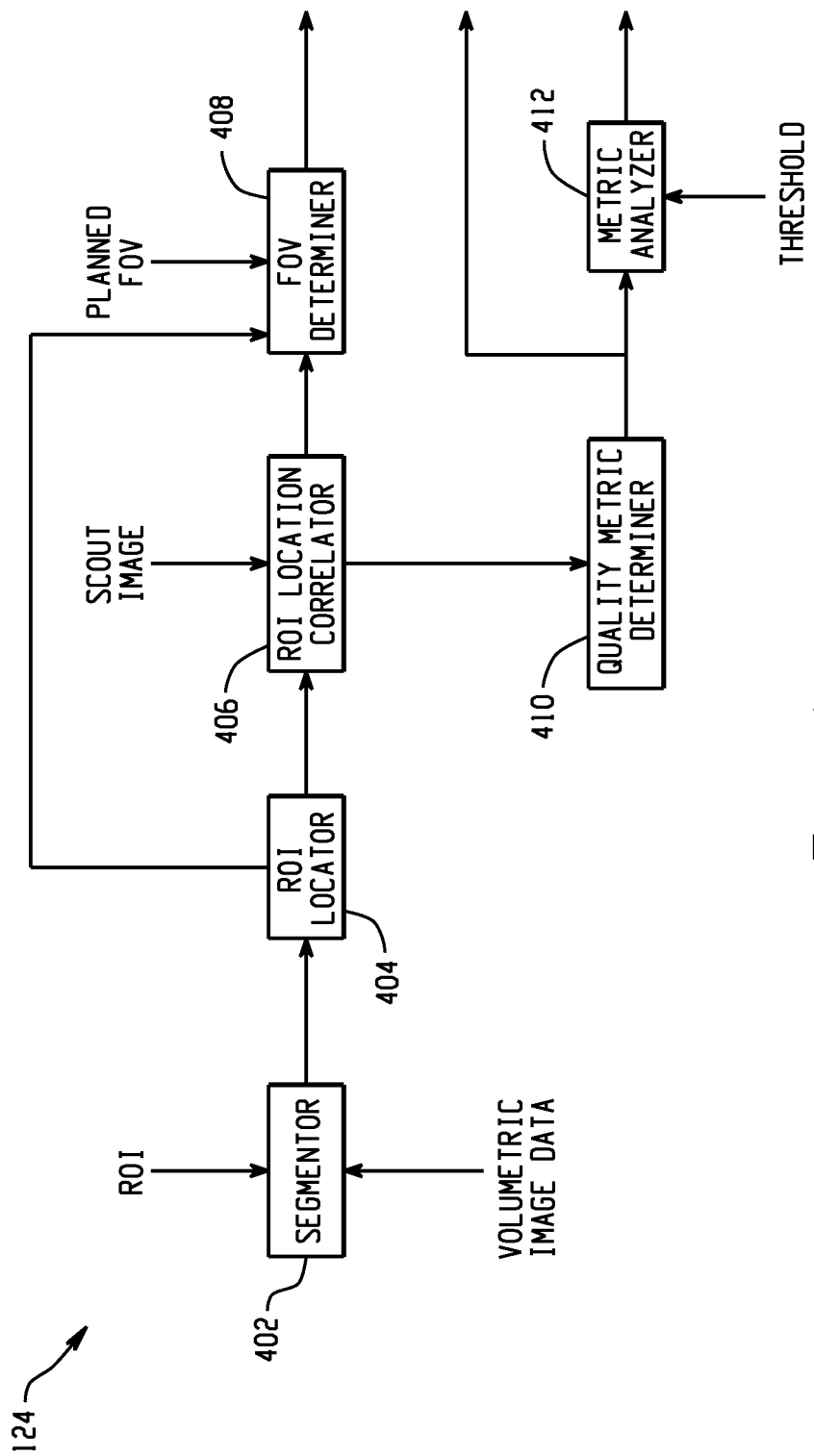

FIGS. 2, 3, and 4 illustrate various examples of the FOV processor of the scan planning apparatus.

Figure 5:
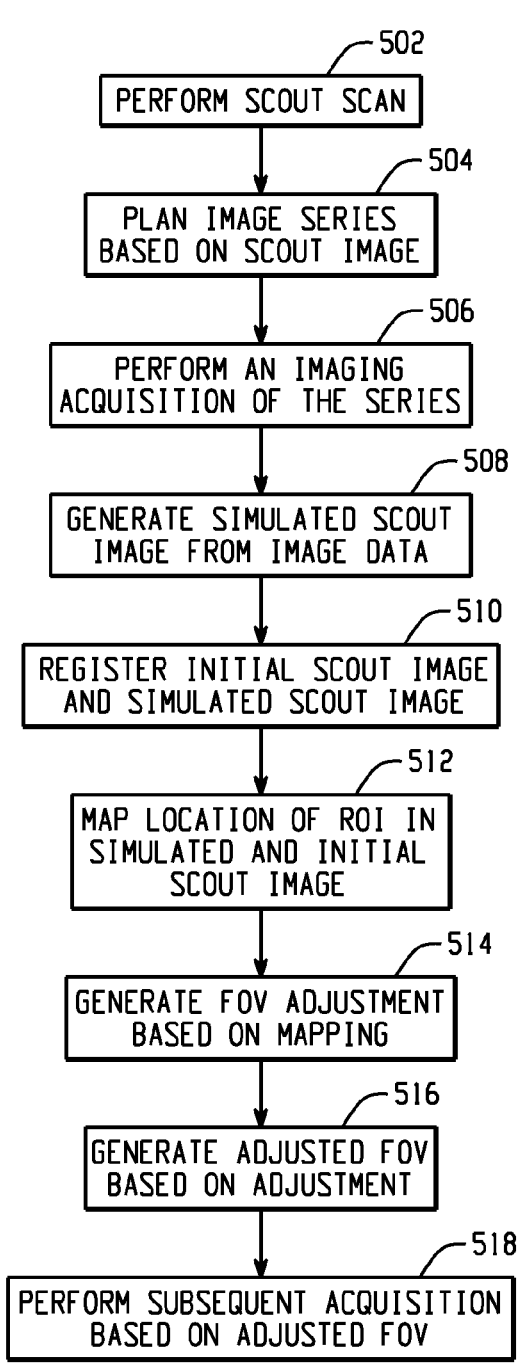
Figure 6:
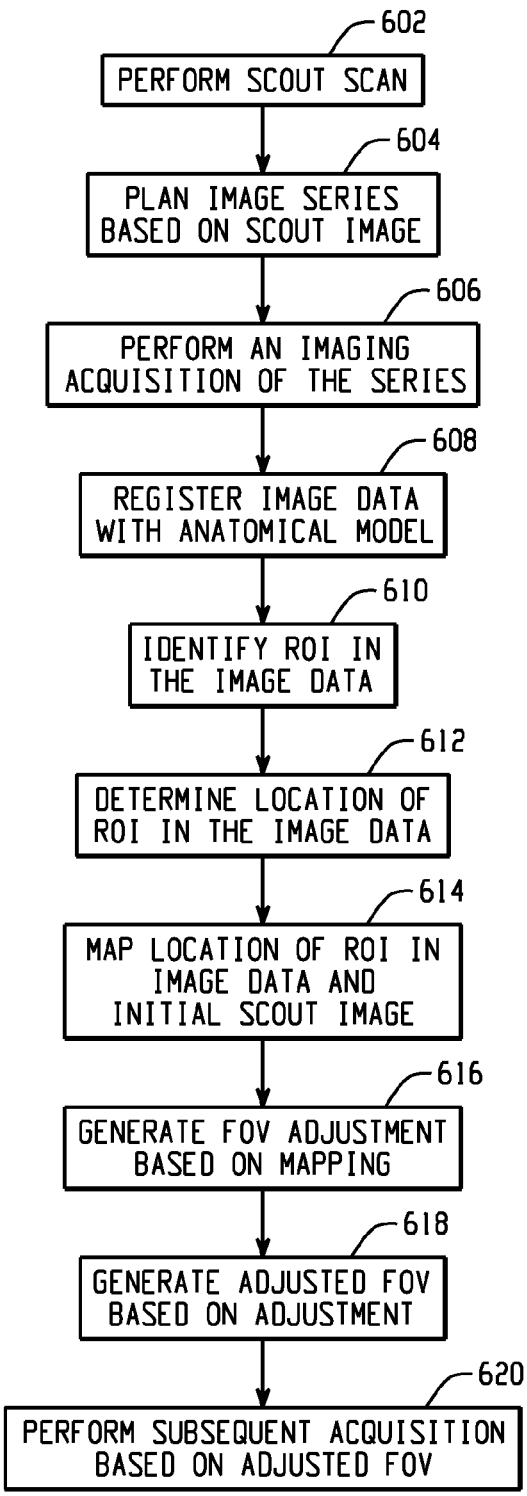
Figure 7:
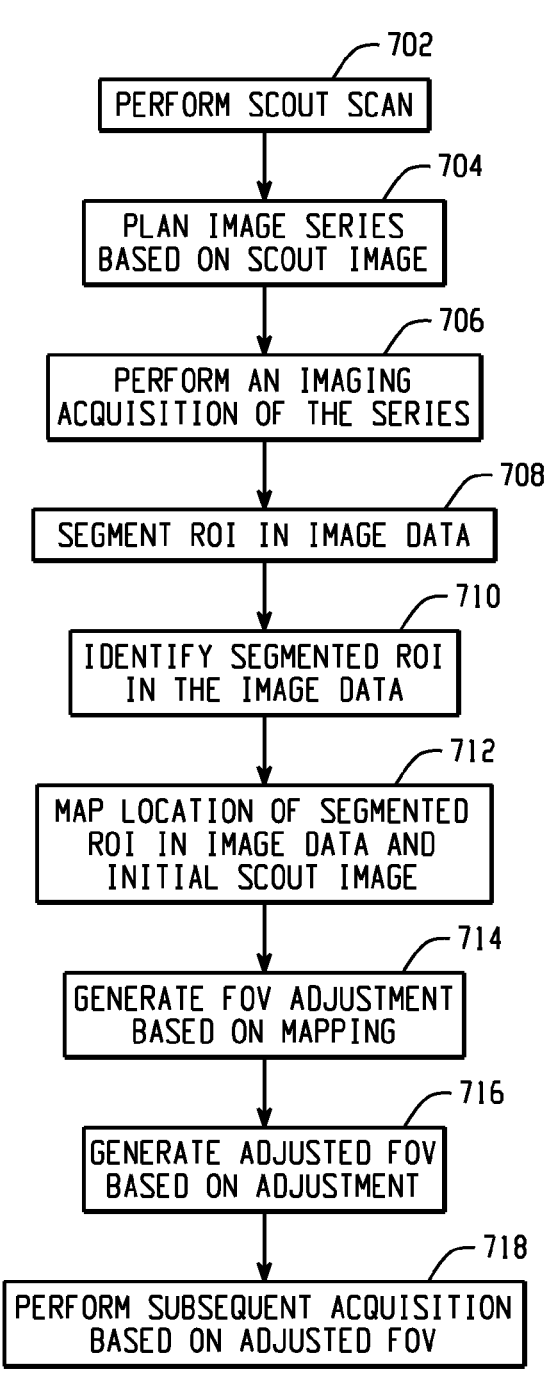

FIGS. 5, 6, and 7 illustrate example methods for adjusting a planned FOV of an image acquisition of a series of image acquisitions.

Figure 8:
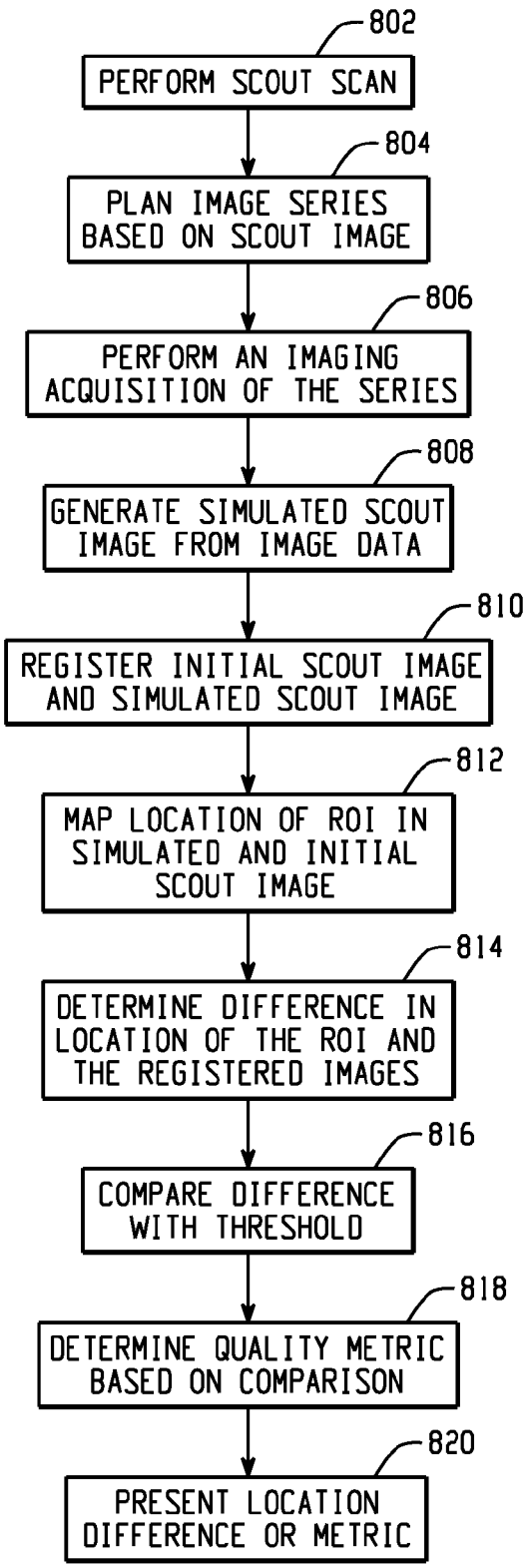

FIGS. 8, 9, and 10 illustrate example methods for validating a planned FOV of an image acquisition of a series of image acquisitions.

Figure 11:
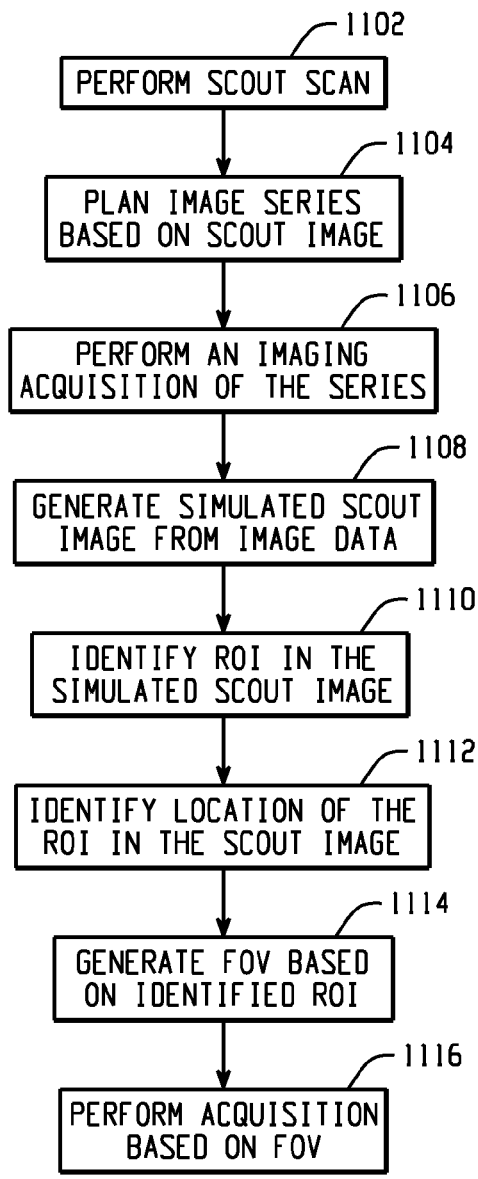
Figure 12:
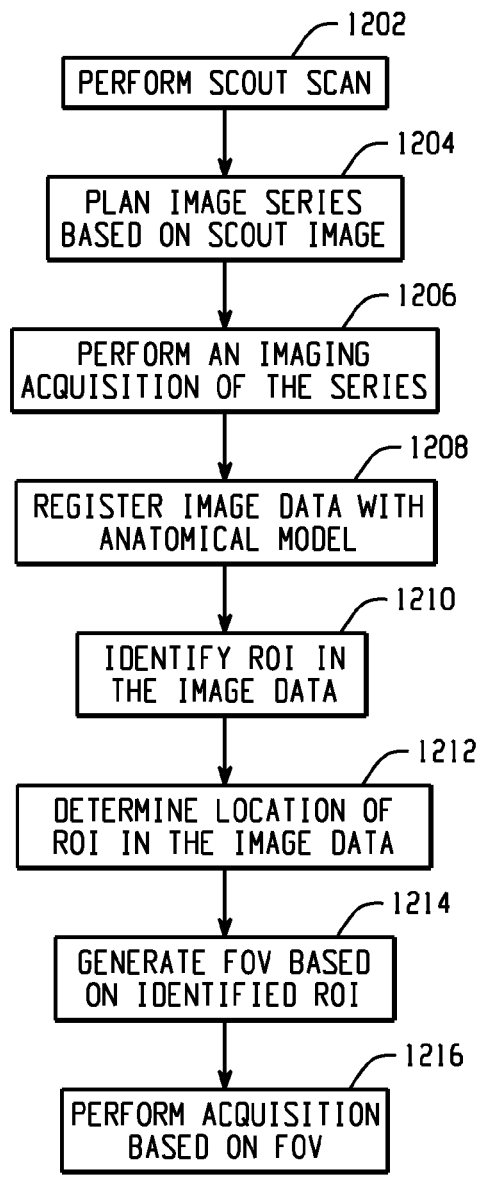
Figure 13:
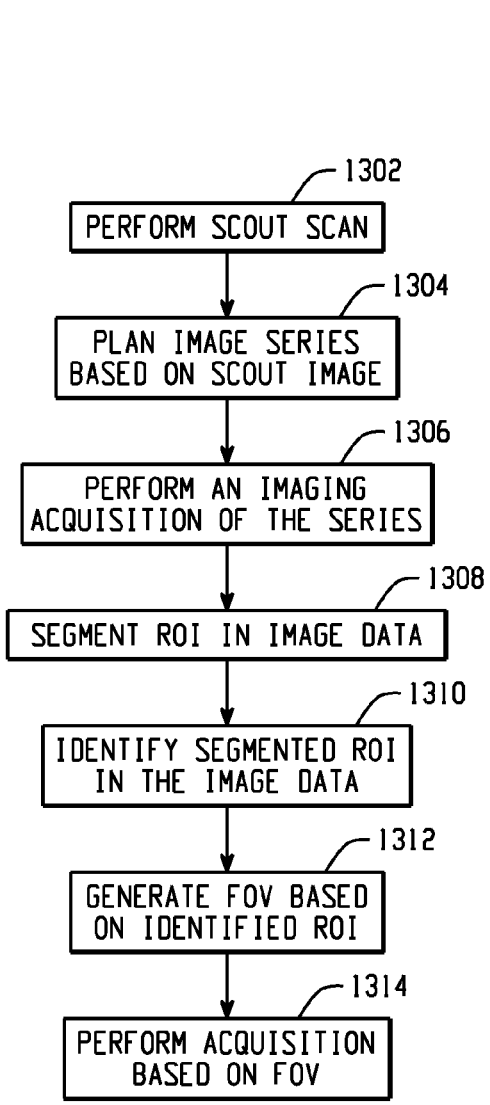

FIGS. 11, 12, and 13 illustrate example methods for determining a scan FOV of an image acquisition of a series of image acquisitions.

Figure 14:
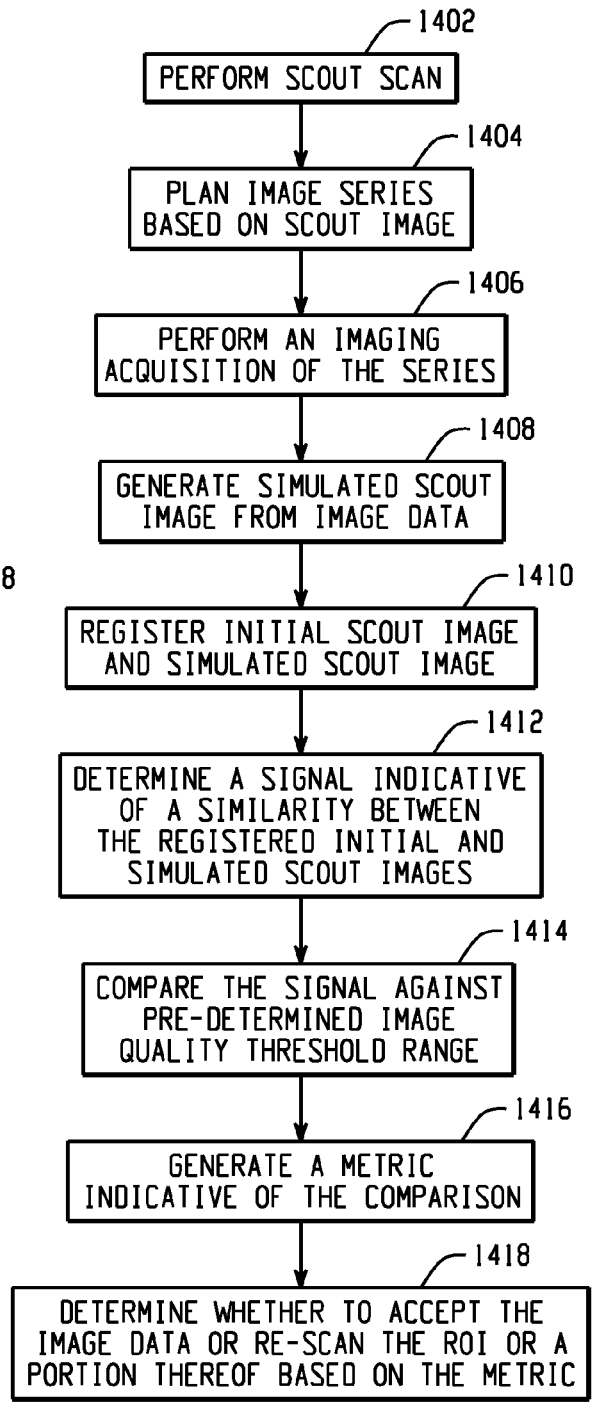

FIGS. 14, 15, and 16 illustrate example methods for validating an image quality a series of image acquisitions.

FIG. 1 illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis 108.

A patient support 110, such as a couch, supports an object or subject such as a human patient in the examination region 106. The patient support 110 facilitates positioning the patient along the x, y, and z-axes, before, during and/or after scanning the patient. In one instance, the patient support 110 moves based on a planned scan field of view (FOV) defined during scan planning to position the patient in the examination region 106 for scanning a region of interest of the patient.

A radiation source 112, such as an x-ray tube, is supported by the rotating gantry 104. The radiation source 112 emits ionizing radiation from a focal spot and the radiation traverses the examination region 106 and an object or subject therein. A source collimator collimates the radiation to form a generally cone, wedge, fan or other shaped radiation beam.

A two-dimensional radiation sensitive detector array 114 subtends an angular arc opposite the radiation source 112 across the examination region 106. The detector array 114 includes a plurality of rows of detectors that extend along the z-axis direction. The detector array 114 detects radiation traversing the examination region 106 and generates projection data indicative thereof.

A reconstructor 116 reconstructs the projection data and generates three-dimensional (3D) volumetric image data indicative thereof. The volumetric image data can be processed to generate one or more images of the object or subject.

A general-purpose computing system or computer serves as an operator console 118. A processor of the console 118 executes computer readable instructions encoded on computer readable storage medium of the console 118, which allows the operator to control operation of the system 100. The console 118 also includes input/output for receiving input and outputting information and a display for presenting information in a human readable format.

A scan planning apparatus 120 generates scan plans that can be implemented by the system 100 and/or other imaging systems.

The scan plan apparatus 120 includes a field of view (FOV) generator 122 that generates one or more scan FOVs for one or more region of interests (ROIs) for a scan plan that includes a series of image acquisitions or procedures. Such FOVs can be generated automatically or in connection with user input based on a pre-scan image such as a scout or pilot image, an image from a lower resolution acquisition, or otherwise. An example of a scan plan with multiple image acquisitions includes a typical a stroke study, which may include a non-contrast brain acquisition, followed by a dynamic CT perfusion acquisition, possibly with two different fields of view, followed by a static CT angiography (CTA) acquisition with additional contrast, followed by a post-contrast late enhancement acquisition, etc.

The scan planning apparatus 120 further includes a FOV processor 124. As described in greater detail below, the FOV processor 124 can adjust a location of a planned scan FOV for an imaging acquisition of a series of acquisitions based on available image related information such as information (e.g., a simulated scout image and/or image data) derived from one or more already performed image acquisitions of the series. Such an adjustment may include adjusting image acquisition start and stop points relative to the position of the patient support 110 in the examination region 106.

In one instance, this allows a planned scan FOV for an image acquisition to be adjusted to compensate for patient movement in which the region of interest of the patient to be scanned moves from a location known from a pre-scan image to a different location in the planned scan FOV or outside of the planned scan FOV. As noted above, the adjustment may include changing the location of the patient support 110 at which scanning begins and/or ends in the scan plan. Consequently, this may mitigate having to have the operator visually inspect the patient to detect patient movement and manually tweak the FOV in the scan plan. This may reduce the time between acquisitions, which may decrease study time and/or reduce the opportunity for patient motion.

Furthermore, the FOV processor 124 can be used to determine a scan FOV for an image acquisition of the series after at least one of the image acquisitions is performed where a scan FOV was not determined for the image acquisition during planning. This scenario may occur, for example, where the region of interest is not visually discernable in the scout image used to generate the plan. In such an instance, some scan FOVs may be determined during planning (when possible) while other scan FOVs are subsequently determined at a stage during an on-going study when acquired data can be used to determine the FOVs.

Furthermore, the FOV processor 124 can validate a planned scan FOV for a particular image acquisition after the image acquisition is performed based on one or more previously performed image acquisitions of the series (e.g., data from the most recent acquisition or other acquisition). In one instance, this allows for determining an amount of movement of a region of interest during an image acquisition (intra-scan motion). This information can be used to determine whether or not the entire region of interest or a sub-portion thereof should be re-scanned due to the movement.

The illustrated scan planning apparatus 120 (including the FOV generator 122 and the FOV processor 124) is part of a computing system that includes one or more processors that execute computer readable instructions encoded in computer readable storage medium thereof. In another embodiment, the scan planning apparatus 120 is part of or integrated with the console 118. In yet another embodiment, the scan planning apparatus 120 is separate from the system 100. In this instance, the scan planning apparatus 120 can be implemented as a single system or in a distributed manner across different systems. The system 100 and the scan planning apparatus 120 can communicate via wired or wireless communications technology.

FIGS. 2-4 illustrate embodiments of the FOV processor 124. Although shown and described as different embodiments in the subject figures, it is to be appreciated that one or more of the embodiments can be combined and/or modified. For these figures, assume that the imaging system 100 is used to obtain a scout or pilot image of an object or subject, the scan planning apparatus 120 is used to create a scan plan therefrom for an anatomical region of interest, and the anatomical region of interest is scanned based on the scan plan.

By way of example, prior to imaging, the object or subject is scanned with the radiation source 112 in a stationary position. A two-dimensional (scout or pilot) image is generated therefrom. The two-dimensional image at least shows an anatomical contour of the portion of the body scanned and the tissue and/or organs therein. From the two-dimensional image, an operator and/or the executing software can create the scan plan, including defining a scan field of view (FOV) with a scan width and a scan length (start and stop positions) covering the anatomical region of interest, setting various parameters such slice thickness, etc. The anatomical region of interest is scanned based on the scan plan. The scout or pilot image, the FOV in the scan plan (the planned FOV), and image data from the scan are used as an input in FIGS. 2-4.

Initially referring to FIG. 2, an example FOV processor 124 in which a simulated scout image is used to adjust a planned scan FOV, determine a scan FOV, and/or validate a planned scan FOV is illustrated. The FOV processor 124 includes an image data processor 202, which receives volumetric image data corresponding to an image acquisition of the series of image acquisitions.

In one instance, the image data processor 202 includes a forward projector that forward projects (e.g., lateral and frontal) the image data and generates a simulated scout image. As noted above, a pre-scan scout image is used to create a scan plan for an anatomical region of interest and then the anatomical region of interest is scanned based on the scan plan. As such, the image data corresponds to the pre-scan scout image. The simulated scout image simulates the pre-scan scout image (based on the resulting image data) that would result in the subject image data. Other techniques for creating such data or data with similar characteristics are also contemplated herein.

Additionally or alternatively, the image data processor 202 includes an image selector that selects a sub-set of images from the image data corresponding to the lower resolution images of the scout images. The image data can be retrieved directly from the reconstructor 116 and/or a storage medium storing image data and can correspond to the last or an earlier image acquisition.

A registration component 204 registers the simulated scout image with the initial scout image used to generate the scan plan and/or a simulated scout image simulated based on image data from a previous image acquisition of the series. Where the scout image is from a lower resolution acquisition, corresponding data from the volumetric image data can be identified and registered with the images from the lower resolution acquisition. The registration may be a rigid or non-rigid (e.g., elastic).

A region of interest (ROI) identifier 206 identifies the scan plan region of interest in the simulated scout image based on the registration and the region of interest.

A ROI location correlator 208 correlates or generates a mapping between the location of the region of interest in the simulated scout image and the location of the region of interest in the initial scout image.

A FOV determiner 210 uses the correlation to adjust (e.g., translate and/or rotate) the planned FOV, or generate an adjusted FOV.

The scan planning apparatus 120 (FIG. 1) conveys the adjusted FOV to the console 118 for a subsequent image acquisition of the series.

In instances in which a FOV has not been defined during planning for at least one of the image acquisitions of the series, the FOV determiner 210 can determine a FOV for a subsequent image acquisition based on simulated FOV and the region of interest. In this instance, the (ROI) identifier 206 identifies the region of interest in the simulated scout image and the FOV determiner 210 determines a FOV for the image acquisition based on the location of the region of interest in the simulated scout image.

A quality metric determiner 212 determines various quality related metrics, including, but not limited to a first metric indicative of a quality of a current image acquisition based on the correlation between the location of the region of interest in the simulated scout image and the location of the region of interest in the initial planning scout image. In one instance, the first metric is indicative of an amount of relative offset between the locations of regions of interest in the two scout images, which corresponds to an amount of movement of the region of interest between the initial planning scout image and the simulated scout image.

The quality metric determiner 212 additionally or alternatively determines a second metric that indicates an image quality of particular image data. In this example, the second metric is based on a similarity between the initial scout image (or a simulated scout image from a previously performed acquisition of the series) and the simulated scout for the current acquisition, independent of the imaged field of view. For example, motion during an acquisition (intra-scan motion) can lead to a motion artifact and lower image quality, even when the initial field of view and the final field of view align. Such motion is reflected in the simulated scout image and can be determined based on the initial or a previously generated scout image.

A metric analyzer 214 analyzes the metric(s) based on a predetermined threshold(s) (e.g., location offset and similarity) and generates a signal(s) indicative of whether or not the metric(s) satisfies the predetermined threshold(s).

As shown, the adjusted FOV, the newly determined FOV, the quality metric(s), the predetermined threshold(s), and/or the signal(s) indicative of whether or not the metric satisfies the predetermined threshold can be conveyed to the console 118, which can display all or a portion of the information. Authorized personnel can accept, reject, and/or modify the scan plan based on this information.

In another embodiment, the quality metric determiner 212 and/or the metric analyzer 214 are omitted. In another embodiment, the FOV determiner 210 is omitted.

Turning to FIG. 3, an example FOV processor 124 in which an anatomical model is used to adjust a planned scan FOV, determine a scan FOV, and/or validate a planned scan FOV is illustrated.

A registration component 302 registers image data from one or more image acquisitions of the series with an anatomical model. Likewise, the registration may be a rigid or non-rigid (e.g., elastic), and the image data can be retrieved by the reconstructor 116 and/or a storage medium storing image data. Registering the most recent image data with the model (e.g., atlas data) may provide the most recent location of the region of interest in the examination region 106 (FIG. 1).

A ROI identifier 304 identifies the scan plan region of interest in the image data based on the registration with the model and the region of interest.

A ROI locator 306 locates the region of interest in the image data.

A ROI location correlator 308 correlates the location of the region of interest in the image data to the location of the region of interest in the scout image.

A FOV determiner 310 uses the correlation to adjust (e.g., translated and/or rotate) the planned FOV, or generate an adjusted FOV.

The scan planning apparatus 120 (FIG. 1) conveys the adjusted FOV to the console 118 for a subsequent image acquisition of the series.

In instances in which a FOV has not been defined during planning for at least one of the image acquisitions of the series, the FOV determiner 310 can determine a FOV for a subsequent image acquisition based on the location of the region of interest in the image data.

A quality metric determiner 312 determines the first and/or second metrics based on the image data and one or both of the initial planning scout image or image data from a previously performed acquisition of the series.

A metric analyzer 314 analyzes the metric(s) based on a predetermined threshold(s) and generates a signal(s) indicative of whether or not the metric(s) satisfies the predetermined threshold(s).

Similarly, the adjusted FOV, the newly determined FOV, the quality metric(s), the predetermined threshold(s), and/or the signal(s) indicative of whether or not the metric satisfies the predetermined threshold can be conveyed to the console 118, which can variously display the information, and authorized personnel can accept, reject, and/or modify the scan plan based on this information.

In another embodiment, the quality metric determiner 312 and/or the metric analyzer 314 are omitted. In another embodiment, the FOV determiner 310 is omitted.

Next at FIG. 4, an example FOV processor 124 in which segmented image data is used to adjust a planned scan FOV, determine a scan FOV, and/or validate a planned scan FOV is illustrated.

A segmentor 402 segments the region of interest from image data for one or more image acquistions of the series. Again, the image data can be retrieved the reconstructor 116 and/or a storage medium storing image data. Segmenting the most recently acquired image data may provide the most recent location of region of interest.

A region of interest locator 404 locates the segmented region of interest in the image data.

A ROI location correlator 406 correlates the location of the segmented region of interest in the image data to the location of the region of interest in the scout image.

A FOV determiner 408 uses the correlation to adjust (e.g., translated and/or rotate) the planned FOV, or generate an adjusted FOV.

The scan planning apparatus 120 (FIG. 1) conveys the adjusted FOV to the console 118 for a subsequent image acquisition of the series.

In instances in which a FOV has not been defined during planning for at least one of the image acquisitions of the series, the FOV determiner 408 can determine a FOV for a subsequent image acquisition based on the location of the segmented region of interest in the image data.

A quality metric determiner 410 determines the first and/or second metrics based on the segmented image data and one or both of the initial planning scout image and/or segmented image data from a previously performed acquisition of the series. Again, such a metric is indicative of intra-scan movement of the patient.

A metric analyzer 412 analyzes the metric(s) based on a predetermined threshold(s) and generates a signal(s) indicative of whether or not the metric(s) satisfies the predetermined threshold(s).

Likewise, the adjusted FOV, the newly determined FOV, the quality metric(s), the predetermined threshold(s), and/or the signal(s) indicative of whether or not the metric satisfies the predetermined threshold can be conveyed to the console 118, which can display the information, and authorized personnel can accept, reject, and/or modify the scan plan based on this information.

In another embodiment, the quality metric determiner 410 and/or the metric analyzer 412 are omitted. In another embodiment, the FOV determiner 408 is omitted.

FIGS. 5-13 illustrate various methods for adjusting a planned scan FOV, validating a planned scan FOV, and/or determining a scan field of view. It is to be appreciated that the acts described in the methods are for explanatory purposes and not limiting. For example, one or more of the methods may include more or less acts, including different acts. In addition, one or more acts of one or more of the methods may occur in a different order that listed. Moreover, one or more of the methods may be combined.

Initially referring to FIG. 5, a method for adjusting a planned scan FOV based on a simulated scout image is illustrated.

At 502, a scout scan is performed.

At 504, a series of image acquisitions is planned based on the scout image, including identifying a region of interest in the series of image acquisitions and defining a scan FOV for the region of interest in the series.

At 506, an image acquisition of the series is performed.

At 508, a simulated scout image is generated based on image data from the performed image acquisition. As discussed herein, the simulated scout image can be generated by forward projection of the image data into the planes acquired during the scout scan or by selecting parts of the image data that have been selected during the scout scan.

At 510, the scout image and the simulated scout image are registered.

At 512, a mapping between a location of the region of interest in the scout image and a location of the region of interest in the simulated scout image is determined.

At 514, the mapping is used to generate a FOV location adjustment (e.g., a translation and/or rotation) to the planned scan FOV of a next imaging procedure of the series of imaging procedures.

At 516, an adjusted FOV is generated for the next image acquisition based on the FOV location adjustment and the planned FOV.

At 518, the next image acquisition is performed based on the adjusted FOV.

For a subsequent image acquisition, the adjusted FOV can be determined based on the initial scout image (as described above), one or more other simulated scout images, or a combination thereof. Image data from one or more performed image acquisition of the series may additionally be used to determine the adjusted scan FOV.

Turning to FIG. 6, a method for adjusting a planned scan FOV based on an anatomical model is illustrated.

At 602, a scout scan is performed.

At 604, a series of image acquisitions is planned based on the scout image, including identifying a region of interest in the series of image acquisitions and defining a scan FOV for the region of interest in the series.

At 606, an image acquisition of the series is performed.

At 608, image data from the image acquisition is registered with an anatomical model or atlas that includes the region of interest.

At 610, the region of interest is identified in the image data based on the registration.

At 612, a location of the region of interest in the image data is determined.

At 614, a mapping between the location of the region of interest in the image data and the location of the region of interest in the scout image is determined.

At 616, the mapping is used to generate an adjustment to the planned scan FOV for a next image acquisition of the series of imaging procedures for the region of interest.

At 618, an adjusted FOV is generated for the next image acquisition based on the FOV location adjustment and the planned FOV.

At 620, the next image acquisition is performed based on the adjusted FOV.

For subsequent image acquisitions, the adjusted FOV can be determined based on image data for one or more performed image acquisitions of the series. An initial scout scan and/or one or more simulated scout scans may additionally be used to determine the adjusted FOV.

Next at FIG. 7, a method for adjusting a planned scan FOV based on segmented image data is illustrated.

At 702, a scout scan is performed.

At 704, a series of image acquisitions is planned based on the scout image, including defining a scan FOV for a region of interest in the series.

At 706, an image acquisition of the series is performed.

At 708, the imaging data is segmented to identify the region of interest in the image data.

At 710, a location of the identified region of interest in the image data is determined.

At 712, a mapping between the location of the region of interest from the segmented image data and the location of the region of interest in the scout image is determined.

At 714, the mapping is used to generate an adjustment to the planned scan FOV for a next image acquisition of the series for the region of interest.

At 716, an adjusted FOV is generated for the next image acquisition based on the FOV location adjustment and the planned FOV.

At 718, the next image acquisition is performed based on the adjusted FOV.

For subsequent image acquisitions, the adjusted FOV can be determined based on segmented image data for one or more performed imaging procedures of the series. An initial scout scan and/or one or more simulated scout scans may additionally be used to determine the adjusted FOV.

FIG. 8 illustrates a method for validating a planned scan FOV based on a simulated scout image.

Acts 802-812 correspond to acts 502-512 of FIG. 5.

At 814, indicia indicative of the difference between the location of the region of interest in the scout image and the location of the region of interest in the simulated scout image is determined.

At 816, the indicia is compared against a predetermined threshold range.

At 818, a metric indicative of whether the indicia is within or outside of the predetermined threshold range is generated based on the comparison.

At 820, at least one of the location difference or the metric, along with the predetermined threshold value, is displayed. The offset can be determined for the entire volume scanned or sub-portions thereof and used to determine whether to repeat the scan of the entire or a sub-portion of the region of interest.

Referring now to FIG. 9, a method for validating a planned FOV based on image data is illustrated.

Acts 902-914 correspond to acts 602-614 of FIG. 6.

At 916, indicia indicative of the difference between the location of the region of interest in the image data and the location of the region of interest in the scout image is determined.

At 918, the indicia is compared against a predetermined threshold range.

At 920, a metric indicative of whether the offset value is within or outside of the predetermined threshold range is generated based on the comparison.

At 922, at least one of the location difference or the metric, along with the predetermined threshold value, is displayed. The offset can be determined for the entire volume scanned or sub-portions thereof and used to determine whether to repeat the scan of the entire or a sub-portion of the region of interest.

With reference to FIG. 10, a method for validating a FOV for a scan based on segmented image data is illustrated.

Acts 1002-1012 correspond to acts 702-712 of FIG. 7.

At 1014, indicia indicative of the difference between the location of the segmented region of interest in the image data and the location of the region of interest in the scout image is determined.

At 1016, the indicia is compared against a predetermined threshold range.

At 1018, a metric indicative of whether the offset value is within or outside of the predetermined threshold range is generated based on the comparison.

At 1020, at least one of the location difference or the metric, along with the predetermined threshold value, is displayed. The offset can be determined for the entire volume scanned or sub-portions thereof and used to determine whether to repeat the scan of the entire or a sub-portion of the region of interest.

FIG. 11 illustrates a method for determining a scan FOV based on a simulated scout image.

Acts 1102-1108 correspond to acts 502-508 of FIG. 5. For act 1104, at least one scan FOV for at least one of the image acquisitions is not defined.

At 1110, the region of interest is identified in the simulated scout image.

At 1112, a location of the region of interest in the simulated scout image is determined.

At 1114, a scan FOV for the region of interest for the at least one image acquisition without a planned scan FOV is determined based on the location of the region of interest in the simulated scout image.

At 1116, the scan FOV is employed for the image acquisition.

In FIG. 12, a method for determining a scan FOV based on an anatomical model is illustrated.

Acts 1202-1212 correspond to acts 602-612 of FIG. 6. For act 1204, at least one scan FOV for at least one of the image acquisitions is not defined.

At 1214, a scan FOV for the region of interest for the at least one image acquisition without a planned scan FOV is determined based on the location of the region of interest in the registered image data.

At 1216, the scan FOV is employed for the image acquisition.

FIG. 13 illustrates a method for determining a scan FOV based on segmented image data.

Acts 1302-1310 correspond to acts 702-710 of FIG. 7.

At 1312, a scan FOV for the region of interest for the at least one image acquisition without a planned scan FOV is determined based on the location of the segmented region of interest in the image data.

At 1314, the scan FOV is employed for the image acquisition.

FIG. 14 illustrates a method for validating image quality based on a scout image.

Acts 1402-1410 correspond to acts 502-510 of FIG. 6.

At 1412, a signal indicative of a similarity between the simulated scout image and the initial scout image (or a simulated scout image determined from a previous acquisition) is determined.

At 1414, the signal is compared against a predetermined image quality threshold range.

At 1416, a metric indicative of whether the similarity is within or outside of the predetermined threshold range is generated based on the comparison.

At 1418, the image quality metric can be presented and used to determine whether to accept the image data or re-scan the region of interest (or a sub-set thereof).

FIG. 15 illustrates a method for validating image quality based on image data.

Acts 1502-1510 correspond to acts 602-610 of FIG. 6.

At 1512, a signal indicative of a similarity between the region of interest in the image data and the region of interest in the initial scout image (or image data from a previous acquisition) is determined.

At 1514, the signal is compared against a predetermined image quality threshold range.

At 1516, a metric indicative of whether the similarity is within or outside of the predetermined threshold range is generated based on the comparison.

At 1518, the image quality metric can be presented and used to determine whether to accept the image data or re-scan the region of interest (or a sub-set thereof).

FIG. 16 illustrates a method for validating image quality based on segmented image data.

Acts 1602-1608 correspond to acts 702-708 of FIG. 7.

At 1610, a signal indicative of a similarity between the segmented image data and the initial scout image (or segmented image data from a previous acquisition) is determined.

At 1612, the signal is compared against a predetermined image quality threshold range.

At 1614, a metric indicative of whether the similarity is within or outside of the predetermined threshold range is generated based on the comparison.

At 1616, the image quality metric can be presented and used to determine whether to accept the image data or re-scan the region of interest (or a sub-set thereof).

The acts described herein may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

Although the above is describe in connection with a CT scanner, it is to be appreciated that the above also applies to non-CT imaging applications in which a pre-scan image is used to plan a series of image acquisitions where patient movement may result in planned FOV no longer being a desired FOV. Examples of such imaging applications include but are not limited to MRI, interventional X-ray, and/or other imaging applications.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   using a pre-scan image to define a scan field of view for a region of interest of a patient to be scanned for at least one image acquisition of a series of image acquisitions of a scan plan;
   performing an image acquisition of the series based on a corresponding scan field of view for the image acquisition; and
   determining, via a processor, a next field of view for a next image acquisition of the series based on available image related data by:
      registering image data from the performed image acquisition with an anatomical model;
      locating the region of interest in the image data based on the registered anatomical model; and
      generating a correlation signal indicative of a correlation between a first location of the region of interest in the image data and a second location of the region of interest in the pre-scan image.

2. The method of claim 1, further comprising:
   adjusting the planned scan field of view for the next image acquisition, based on the correlation signal, to determine an updated next field of view for the next image acquisition.

3. The method of claim 2, wherein adjusting the planned scan field of view for the next image acquisition includes at least one of translating or rotating the planned scan field of view based on the correlation signal.

4. The method of claim 1, wherein the scan plan does not include a planned scan field of view for the next image acquisition, and further comprising:
   generating a simulated pre-scan image based on image data from the image acquisition;
   determining a location of the region of interest in the simulated pre-scan image; and
   determining the next field of view for the next image acquisition of the series based on the location of the region of interest in the simulated pre-scan image.

5. The method of claim 4, wherein the adjusted planned scan field of view compensates for movement of the region of interest due to patient motion with respect to the planned scan field of view.

6. The method of claim 1, wherein the scan plan includes a planned scan field of view for the next image acquisition.

7. The method of claim 6, further comprising:
   adjusting the planned scan field of view, based on the correlation signal, to determine an updated next field of view for the next image acquisition.

8. The method of claim 1, wherein the scan plan includes a planned scan field of view for the next image acquisition, and further comprising:
   segmenting image data from the image acquisition to locate the region of interest in the image data; and
   generating a correlation signal indicative of a correlation between a first location of the region of interest in the segmented image data and a second location of the region of interest in the pre-scan image.

9. The method of claim 8, further comprising:
   adjusting the planned scan field of view, based on the correlation signal, to determine an updated next field of view for the next image acquisition.

10. The method of claim 1, wherein the scan plan does not include a planned scan field of view for the next image acquisition, and further comprising:
    segmenting image data from the image acquisition to locate the region of interest in the image data; and
    determining the next field of view for the next image acquisition of the series based on the location of the region of interest in segmented the image data.

11. The method of claim 1, further comprising:
    determining a quality metric based on the correlation signal;
    generating indicia indicative of whether the quality metric satisfies a predetermined quality threshold; and
    displaying at least one of the quality metric or the indicia.

12. A scan planning apparatus, comprising:
    a field of view generator that defines a scan field of view for a region of interest of a patient for at least one image acquisition of a series of image acquisitions of a scan plan based on a pre-scan image; and
    a field of view processor that determines a next field of view for a next image acquisition of the series based on available image related data by:
       identifying the region of interest in the image data based on a registration;
       locating the region of interest in the image data; and
       generating a correlation signal indicative of a correlation between a location of the region of interest in the pre-scan image and a location of the region of interest in the image data;
       wherein the field of view processor adjusts the planned next scan field of view for the next image acquisition based on the correlation signal.

13. The apparatus of claim 12, wherein the available image related data is one or more of a scout image or image data.

14. The apparatus of claim 12, further comprising:
    a forward projector that forward projects image data from at least one of the image acquisitions to generate a simulated pre-scan image, wherein the field of view processor determines the next scan field of view for the next image acquisition based on a location of the region of interest in the simulated pre-scan image.

15. The apparatus of claim 12, wherein the field of view processor determines a next scan field of view for the next image acquisition based on the registration of the image data and the anatomical model when the next image acquisition does not have a planned scan field of view.

16. The apparatus of claim 12, further comprising:
a segmentor that segments the region of interest in image data from at least one of the image acquisitions;
wherein the field of view processor adjusts a planned next scan field of view for the next image acquisition based on the region of interest in the segmented image data.

17. The apparatus of claim 16, further comprising:
a region of interest identifier that identifies the region of interest in the segmented image data based on the registration;
a region of interest locator that locates the region of interest in the segmented image data; and
a region of interest location correlator that generates a correlation signal indicative of a correlation between a location of the region of interest in the pre-scan image and a location of the region of interest in the segmented image data,
wherein the field of view processor adjusts the planned next scan field of view for the next image acquisition based on the correlation signal.

18. The apparatus of claim 16, wherein the field of view processor determines a next scan field of view for the next image acquisition based on the segmented imaged data when the next image acquisition does not have a planned scan field of view.

19. The apparatus of claim 12, further comprising:
a quality metric determiner that determines a quality metric based on the correlation signal; and
a metric analyzer that generates indicia indicative of whether the quality metric satisfies a predetermined quality threshold, wherein at least one of the metric or the indicia is displayed.

20. A method, comprising:
using a pre-scan image to define a scan field of view for a region of interest of a patient to be scanned for at least one image acquisition of a series of image acquisitions of a scan plan;
performing an image acquisition of the series based on a corresponding scan field of view for the image acquisition; and
determining, via a processor, a next field of view for a next image acquisition of the series based on available image related data by:
segmenting image data from the image acquisition to locate the region of interest in the image data; and
generating a correlation signal indicative of a correlation between a first location of the region of interest in the segmented image data and a second location of the region of interest in the pre-scan image.

* * * * *